(12) United States Patent
Schildkraut et al.

(10) Patent No.: US 7,418,079 B2
(45) Date of Patent: Aug. 26, 2008

(54) SYSTEM FOR THE REAL-TIME DETECTION OF TARGETS FOR RADIATION THERAPY

(75) Inventors: Jay S. Schildkraut, Rochester, NY (US); Mark D. Bedzyk, Pittsford, NY (US); Shoupu Chen, Rochester, NY (US); Timothy J. Wojcik, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 11/419,848

(22) Filed: May 23, 2006

(65) Prior Publication Data

US 2007/0274446 A1 Nov. 29, 2007

(51) Int. Cl.
*A61N 5/10* (2006.01)
*H05G 1/02* (2006.01)
*H05G 1/00* (2006.01)

(52) U.S. Cl. .................. 378/65; 378/197; 378/208

(58) Field of Classification Search ............ 378/4, 378/15, 17, 19, 20, 146, 193, 195–198, 62–65, 378/208

See application file for complete search history.

(56) References Cited

U.S. PATENT DOCUMENTS

| 5,471,516 A | 11/1995 | Nunan |
| RE36,415 E * | 11/1999 | McKenna ................ 378/4 |
| 5,997,176 A * | 12/1999 | Fairleigh ............... 378/196 |
| 6,242,743 B1 * | 6/2001 | DeVito et al. ......... 250/363.05 |
| 6,778,850 B1 | 8/2004 | Adler et al. |
| 6,888,919 B2 | 5/2005 | Graf |
| 6,914,949 B2 * | 7/2005 | Richards et al. ......... 375/346 |
| 6,914,959 B2 * | 7/2005 | Bailey et al. ............ 378/65 |
| 2004/0184579 A1 * | 9/2004 | Mihara et al. ........... 378/65 |

* cited by examiner

*Primary Examiner*—Irakli Kiknadze

(57) ABSTRACT

A method and apparatus for delivering therapeutic radiation (112) to a radiotherapy target (119) in a patient (114) includes a diagnostic X-ray source (124, 125) connected to a treatment couch (116), facing a first side of the patient. An imaging device (118) is connected to the treatment couch facing a second side of the patient. The diagnostic X-ray source and the imaging device move in lockstep with movement of the treatment couch. The patient is in a fixed position relative to the treatment couch.

19 Claims, 16 Drawing Sheets

SYSTEM FOR THE REAL-TIME DETECTION OF TARGETS FOR RADIATION THERAPY

CROSS REFERENCE TO RELATED APPLICATIONS

Reference is made to commonly-assigned copending U.S. patent application Ser. No. 11/039,422, filed Jan. 20, 2005, entitled RADIATION THERAPY METHOD WITH TARGET DETECTION, by Schildkraut et al.; and U.S. patent application Ser. No. 11/221,133, filed Sep. 7, 2005, entitled ADAPTIVE RADIATION THERAPY METHOD WITH TARGET DETECTION, by Schildkraut et al., the disclosures of which are incorporated herein.

FIELD OF THE INVENTION

The invention relates generally to radiation therapy systems in which the region of the radiation therapy target is imaged as part of the radiation treatment.

BACKGROUND OF THE INVENTION

In radiation therapy a high dose of radiation is applied to cancerous tissue in order to destroy it or to at least slow its growth. It is critical to accurately apply the radiation so that the target receives most of the dose and surrounding healthy tissue is spared. For this reason, imaging systems have been incorporated into radiation treatment systems in order to determine if the treatment target is in the correct location when the patient is positioned relative to the treatment beam. Also, since the target may move due to respiration and other physiological processes, even when the patient remains stationary, it is desirable to obtain images of the target immediately before and during radiation treatment. A number of inventions have been directed at imaging the target before or during radiation treatment.

One means of obtaining an image of the target region is to use the therapeutic beam as the imaging source to create a portal image. The drawback of this approach is that portal images have very low contrast due to the high energy of the therapeutic beam. U.S. Pat. No. 5,471,516 solves this problem by incorporating a lower energy diagnostic X-ray source into the treatment head to produce a diagnostic portal image.

U.S. Pat. No. 6,888,919 discloses a radiotherapy machine with a first pivotal gantry that contains a therapeutic radiation source and a second pivotal gantry that contain opposing diagnostic X-ray source and imager. The diagnostic radiographic imaging unit can be rotated around the patient to provide a data set that can be used to produce a three-dimensional reconstruction of the region around the target.

U.S. Pat. No. 6,778,850 discloses a radiotherapy machine with two diagnostic X-ray sources mounted above the treatment couch that capture images of the target region from different perspectives. The simultaneously captured images are used to create a three-dimensional mapping of the target region.

U.S. Pat. No. 6,914,959 discloses a combined radiotherapy and CT imaging system. The CT system can be used to capture planning images and images of the target during treatment. In this way, the patient need not be moved between the planning and treatment phase.

A shortcoming of present methods of imaging a radiation therapy target is that they do not enable the capture of an image of the target region in which detectability of the target is optimal for all positions of the treatment couch. Furthermore, some of the present methods require that the diagnostic source be moved in order to capture several images of the target region that may be used to reconstruct a three-dimensional image. This can preclude near real-time target localization.

An object of the present invention is to provide an imaging system that can capture images of a radiation therapy target region, using desired capture conditions for which the radiation target can be detected, without the use of internal markers. Another object of the present invention is to maintain the desired capture conditions when the treatment couch is moved. Another object of the present invention is to obtain images in which the target is detectable without the need to move the imaging source or detector during the image acquisition process so that the target can be localized in near real-time.

SUMMARY OF THE INVENTION

In commonly-assigned copending U.S. patent application Ser. No. 11/039,422 it is disclosed how a three-dimensional planning image is used to determine desired capture conditions for radiographic images in which the radiation target can be directly detected. Commonly-assigned copending U.S. patent application Ser. No. 11/221,133 discloses a means of identifying a radiation target in a captured radiographic image based on characteristics of the target in a digitally reconstructed radiograph (DRR).

In the present invention a diagnostic X-ray source and an imaging device are connected to a treatment couch so that desired capture conditions are maintained throughout the movement of the treatment couch.

The invention and its objects and advantages will become more apparent in the detailed description of the preferred embodiment presented below.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 10A is an overhead view of radiotherapy system with both diagnostic X-ray sources turned on.

FIG. 10B is a frontal view of radiotherapy system with both diagnostic X-ray sources turned on.

FIG. 11A is an overhead view of radiotherapy system with left diagnostic X-ray source turned off and right source turned on.

FIG. 11B is a frontal view of radiotherapy system with left diagnostic X-ray source turned off and right source turned on.

FIG. 12A is an overhead view of radiotherapy system with both diagnostic X-ray sources turned on.

FIG. 12B is a frontal view of radiotherapy system with both diagnostic X-ray sources turned on.

FIG. 14A is an overhead view of radiotherapy system with both diagnostic X-ray sources turned on.

FIG. 14B is a frontal view of radiotherapy system with both diagnostic X-ray sources turned on.

DETAILED DESCRIPTION OF THE INVENTION

The present invention will be directed in particular to elements forming part of, or in cooperation more directly with the apparatus in accordance with the present invention. It is to be understood that elements not specifically shown or described may take various forms well known to those skilled in the art.

Figure 1:
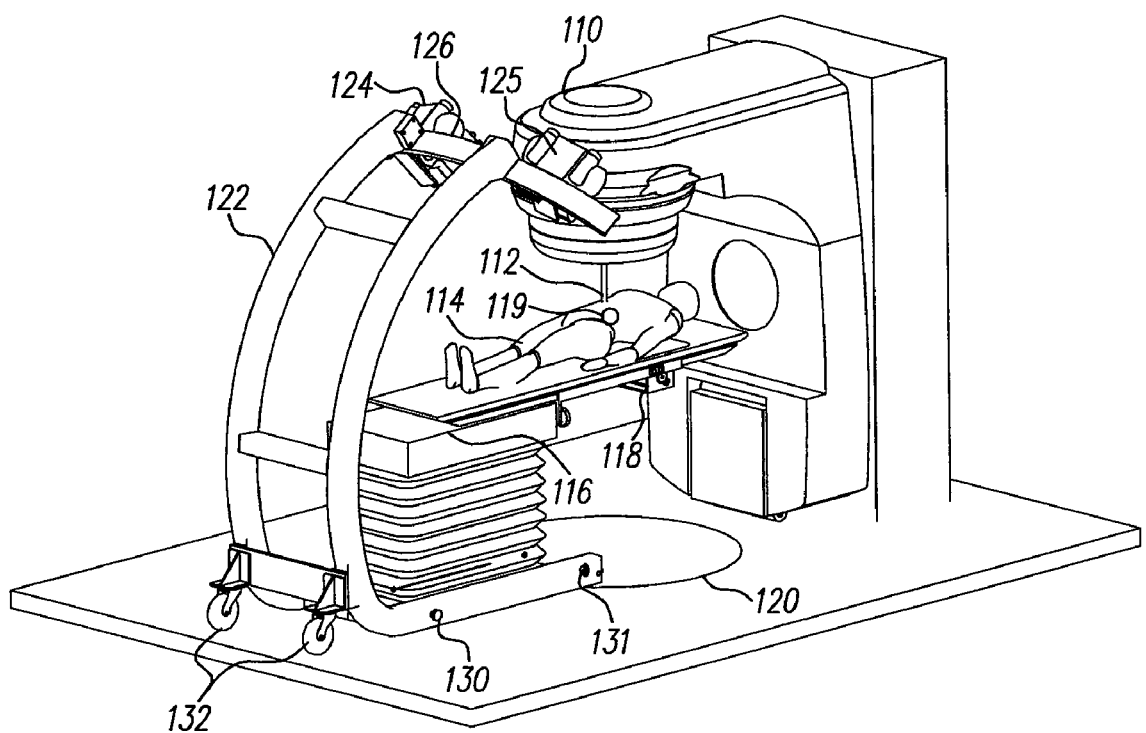
FIG. 1 is a diagram of a radiotherapy system in which the treatment couch is connected to an imaging device and a diagnostic X-ray source.

FIG. 1 shows a radiotherapy system in which the treatment couch is connected to an imaging device and a diagnostic X-ray source. Radiotherapy gantry 110 produces a therapeutic radiation beam 112 that is aimed at a radiotherapy target 119 inside the body of patient 114. The patient lies on treatment couch 116. The treatment couch is attached to floor pivot 120 which rotates the treatment couch in order to change the position of the patient relative to the therapeutic radiation beam. Connected to the treatment couch is imaging device 118. Also connected to the treatment couch is X-ray source frame 122 which supports left diagnostic X-ray source 124 and right diagnostic x-ray source 125. The diagnostic X-ray source moves on X-ray source guide rail 126 in order to obtain a desired view of the radiotherapy target 119 for which the target is detectable in images captured with a diagnostic imaging unit consisting of a diagnostic X-ray source and imaging device. The X-ray source frame is connected to the treatment couch in a precise location by the use of threaded holes for side locating feature 130 and retractable pins for axial locating feature 131. The imaging source frame has attached rear wheels 132 which facilitate its attachment to or removal from the treatment couch. When the X-ray source frame is fixed in place the wheels 132 are lifted so that they do not drag along the floor when the treatment couch is moved by floor pivot 120.

Figure 2:
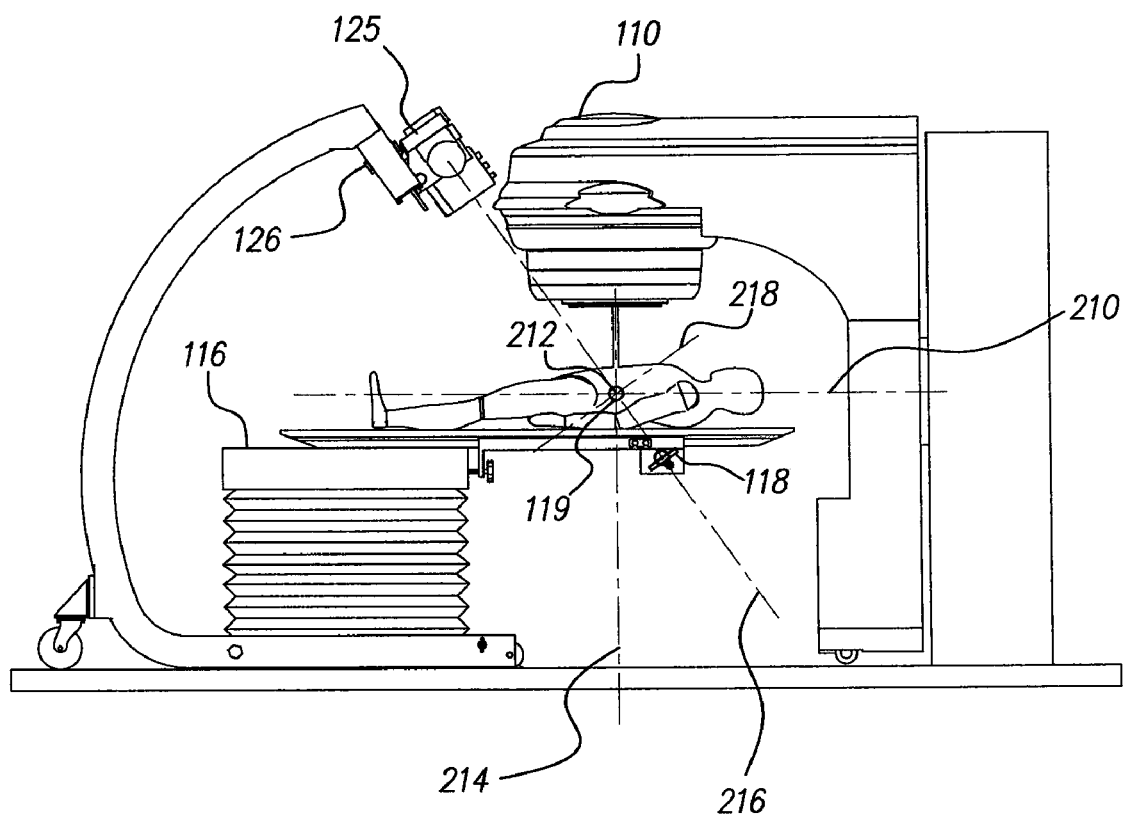
FIG. 2 is a diagram of a radiotherapy system in which the treatment couch is connected to an imaging device and a diagnostic X-ray source along with axes of rotation of moving parts of the system.

FIG. 2 shows a radiotherapy system in which the treatment couch is connected to an imaging device 118 and a diagnostic X-ray source 125 along with axes of rotation of moving parts of the system. The radiotherapy gantry 110 rotates around axis 210. The point on this axis that intersects the center of the treatment beam 216 is the radiotherapy isocenter 212. The treatment couch 116 rotates about the axis 214 because of its attachment to the floor pivot (see item 120 in FIG. 1). The right diagnostic X-ray source 125 rotates around axis 218 when it moves on guide rail 126. The guide rail has the shape of an arc with a center at the radiotherapy isocenter when the X-ray source frame is properly connected to the treatment couch.

Figure 3:
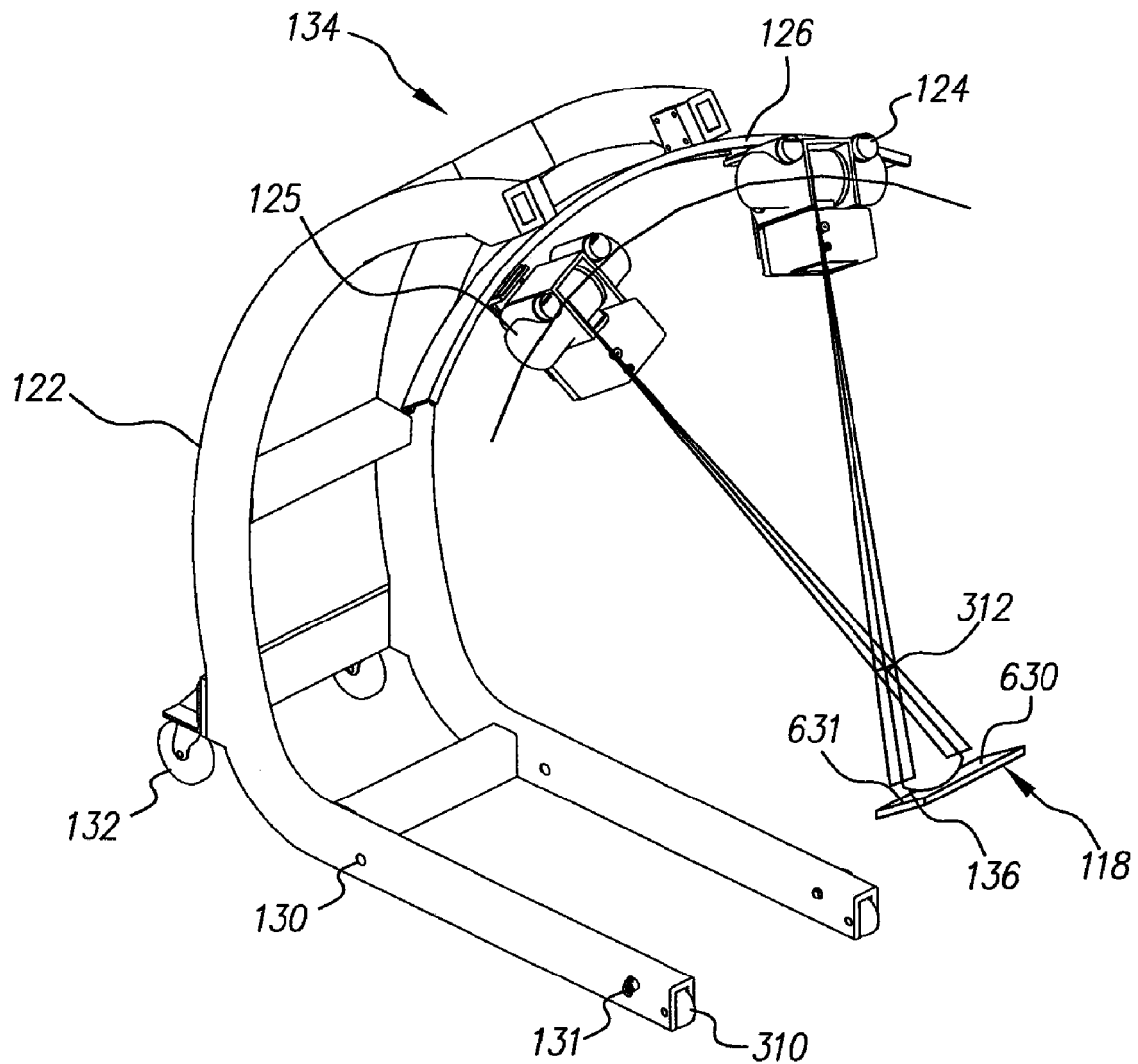
FIG. 3 is a diagram of the diagnostic X-ray source assembly.

FIG. 3 shows the diagnostic X-ray source frame and imaging device when not connected to the treatment couch. The diagnostic X-ray sources 124 and 125 move on guide rail 126. For all locations on the guide rails the sources remain pointed at diagnostic X-ray isocenter 312. This movement provides a means to change the azimuthal angle of a source relative to the patient. When the diagnostic X-ray source frame is connected to the treatment couch the diagnostic X-ray isocenter 312 and the radiotherapy isocenter (see item 212 in FIG. 2) are collocated. The imaging device 118 is shown along with an X-ray beam from source 124 incident on the right side of the imaging device 631 and an X-ray beam from source 125 incident on left side of imaging device 630. The X-ray beams from the two sources form the focal surface 136. Also shown in FIG. 3 are X-ray source frame front wheels 310 which facilitate the movement of the frame to and from connection to the treatment couch.

Figure 4:
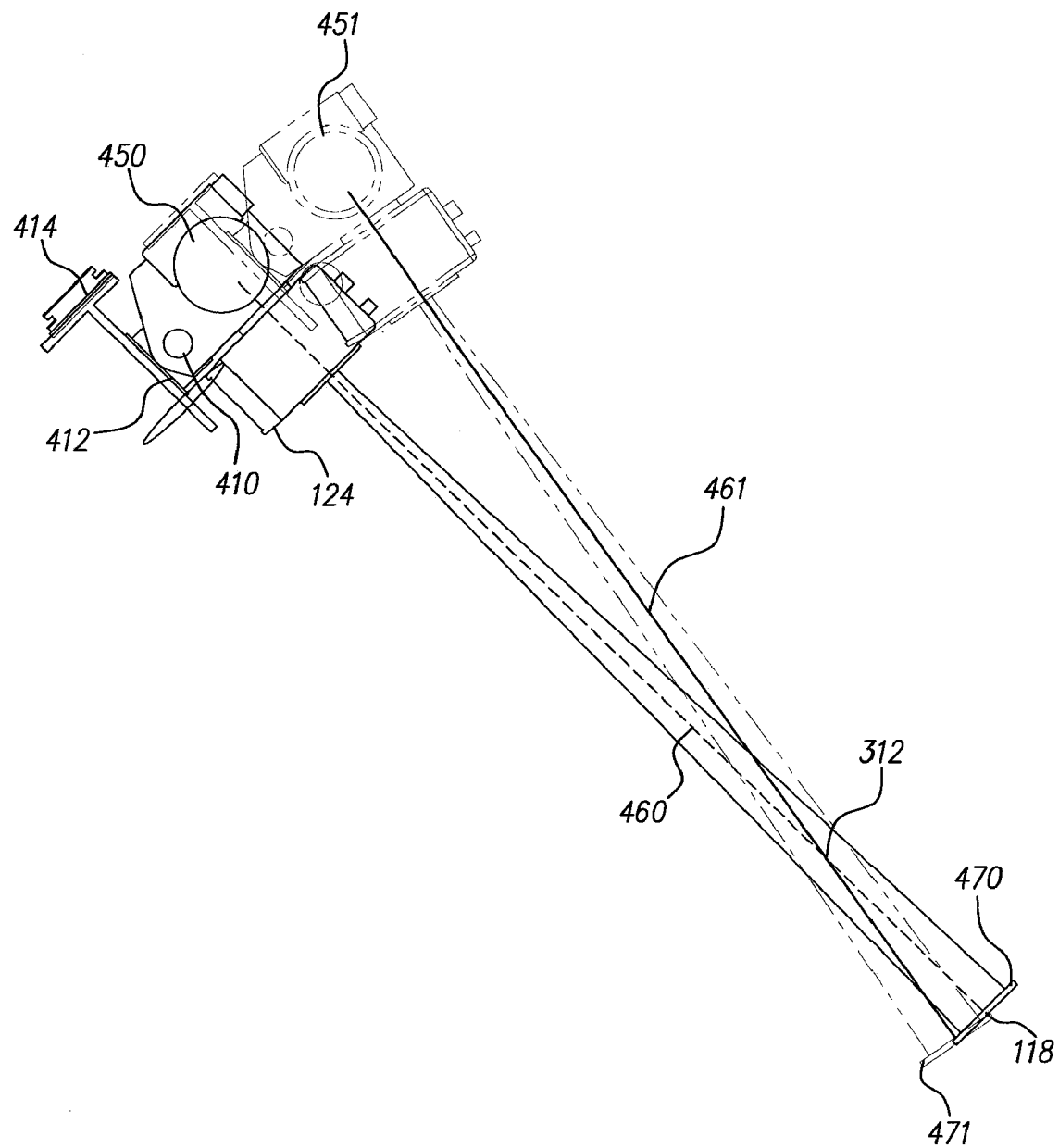
FIG. 4 is a diagram of the vertical and tilt motion of a diagnostic X-ray source.

In addition to the ability to change the azimuthal angle of a diagnostic X-ray source by movement on the guide rail 126, the height may change as well. FIG. 4 shows the mechanism for changing the height of a source that maintains the location of the diagnostic X-ray isocenter 312. The source 124 tilts on pivot 410 and translates on focus carriage 412 and vertical carriage 414. When the source is in location 450 it produces beam 460 that impinges on imaging device 118 when it is in position 470. When the source is in location 451 it produces beam 461 that impinges on imaging device 118 when it is in position 471. In both cases the diagnostic X-ray beam passes through isocenter 312. In one embodiment of this invention, the imaging device 118 is moved and tilted in order to remain in the path of the beam and maintain the beam at normal incidence. Alternatively, the imaging device can be oversized so that the X-ray beam remains in the field of view of the imaging device throughout the range of motion of the source.

Figure 5:
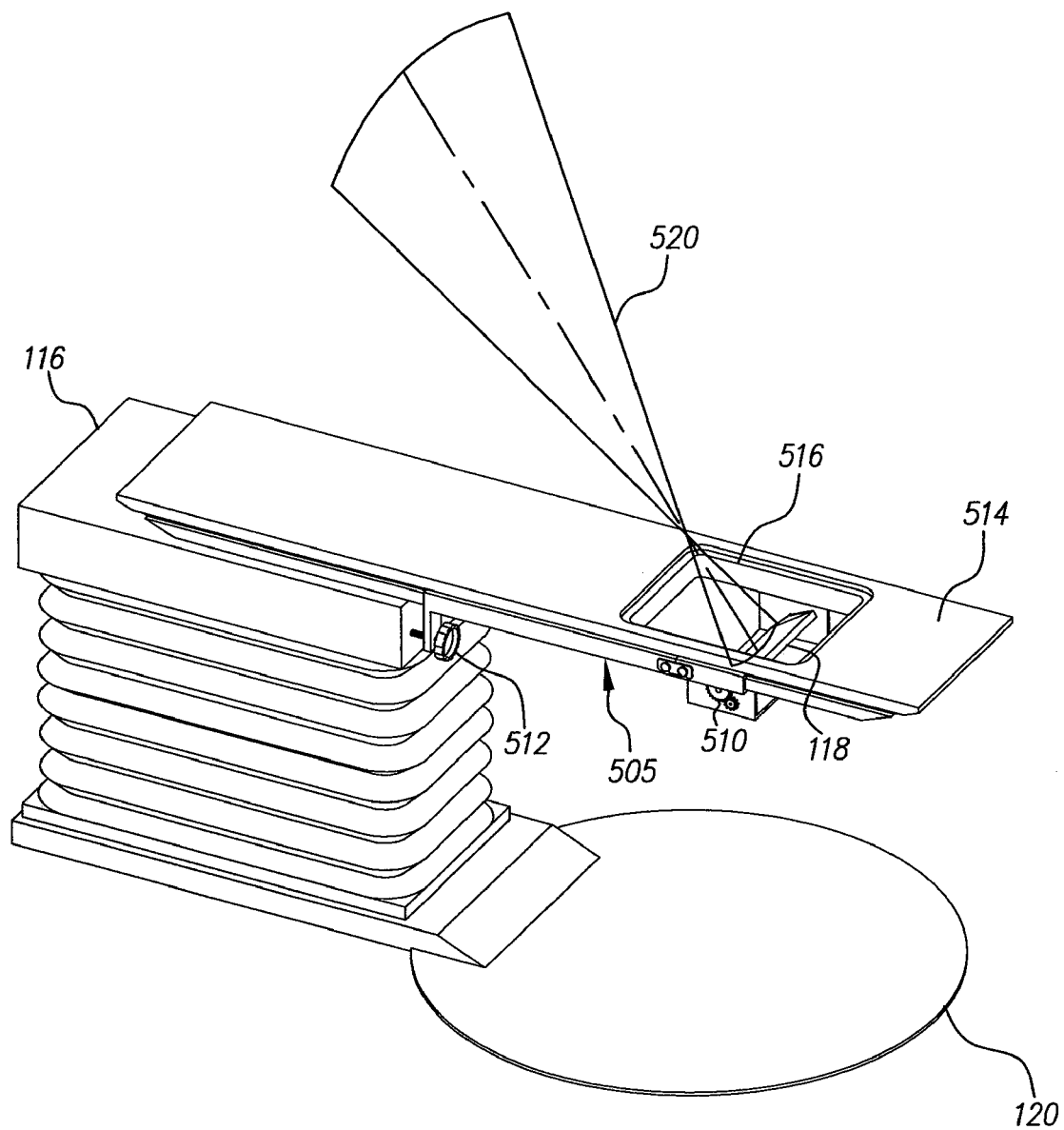
FIG. 5 is a diagram of a treatment couch with an imaging device assembly.

A treatment couch with connected imaging device is shown in FIG. 5. Attached to the top couch top 514 is imaging device assembly 505. The location of the imaging device assembly can be adjusted by knob 512. The tilt of the imaging device 118 is changed by imaging device angular adjustment mechanism 510. In the case that the couch top is not transparent to diagnostic x-rays, an X-ray transparent window 516 is provided. X-ray beams 520 from the diagnostic X-ray sources pass through the window and are incident on the imaging device. In an embodiment of this invention the imaging device 118 is on top of the couch top 514. In this case the imaging device is between the patient and the treatment couch. In addition, the imaging device may be flexible so that it is less easily damaged and can be shaped to best image the diagnostic X-ray sources.

Figure 6:
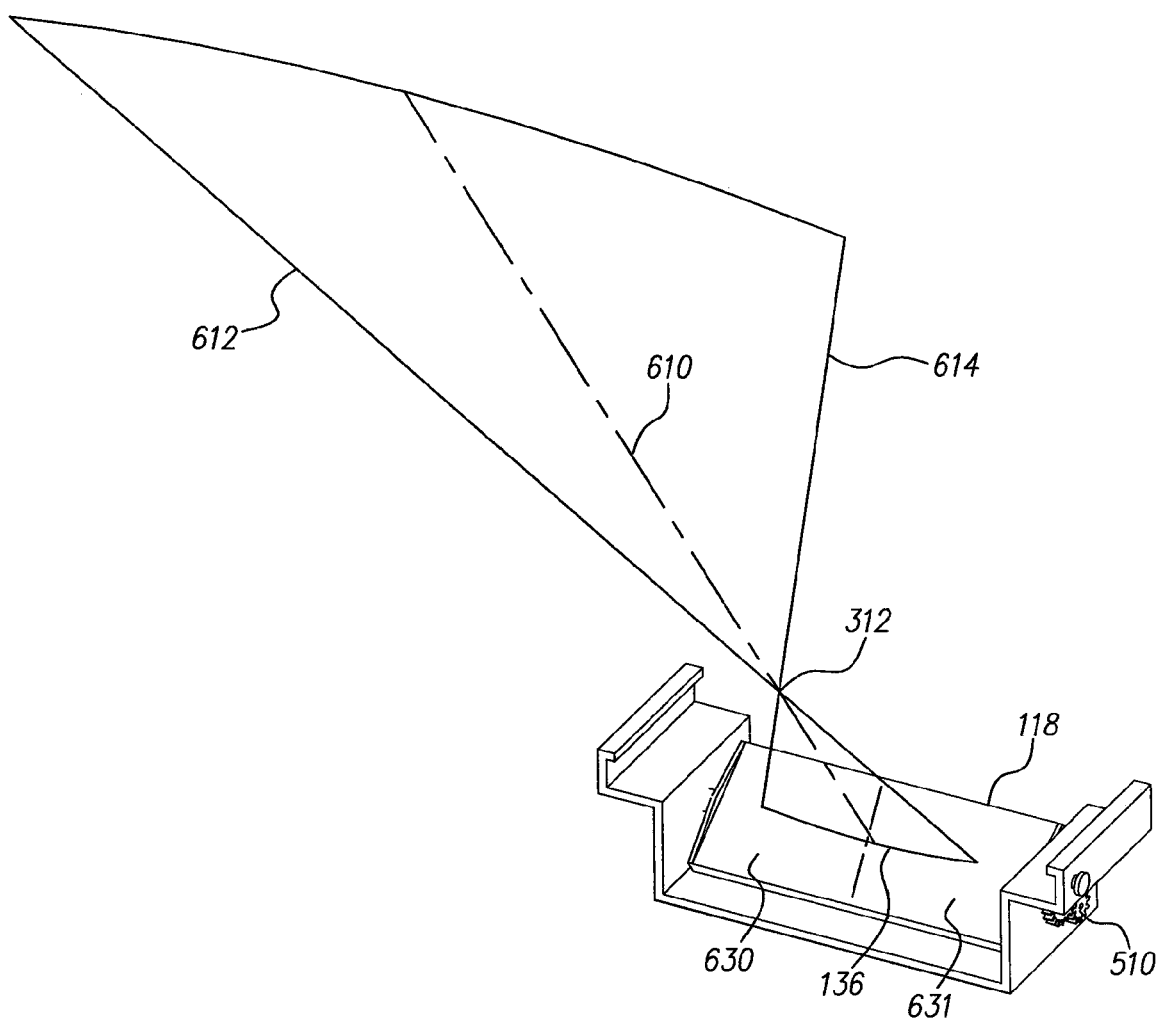
FIG. 6 is a diagram of a flat imaging device.
Figure 7:
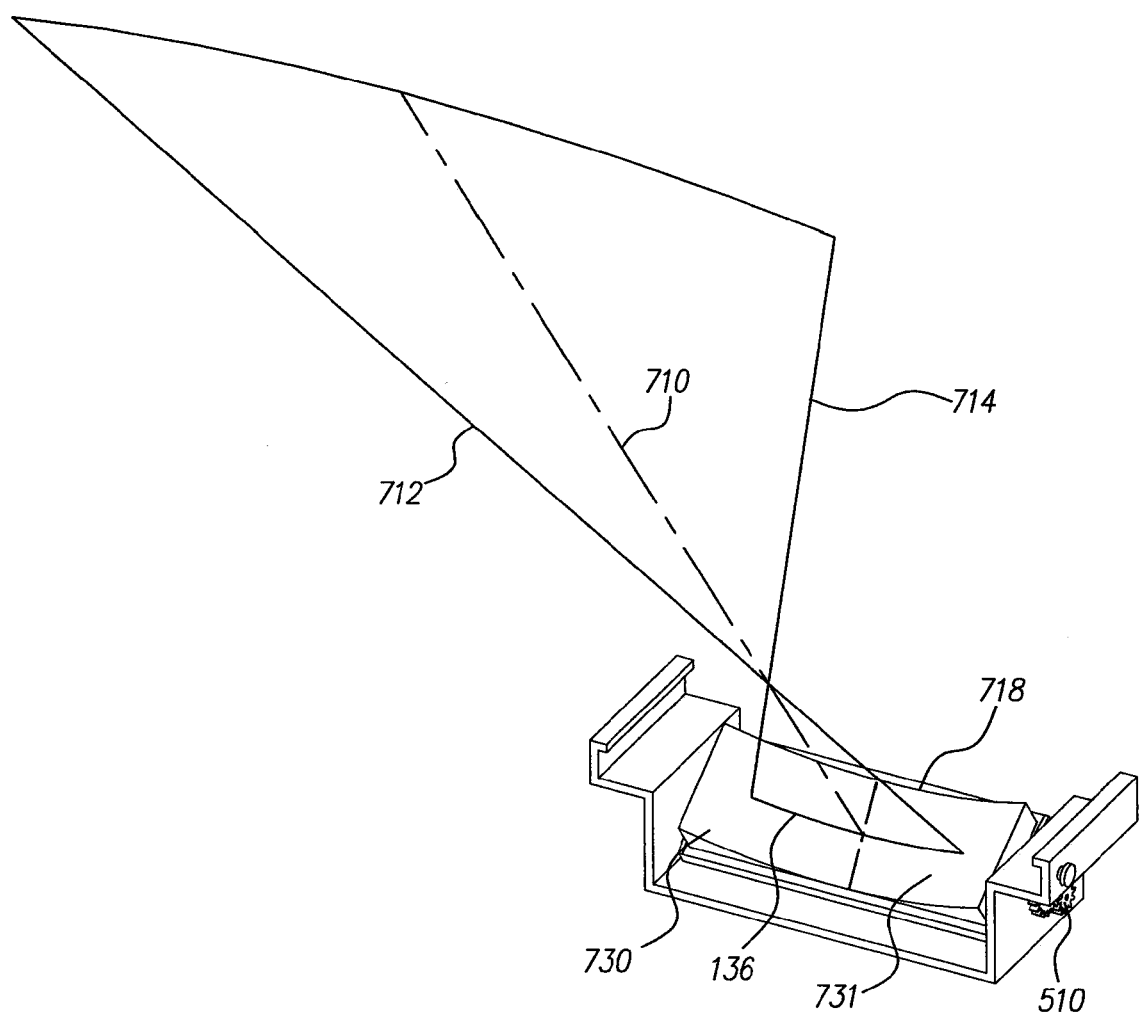
FIG. 7 is a diagram of a curved imaging device.

FIG. 6 shows a flat imaging device 118 and X-rays beams 610, 612, and 614 that are incident on the imaging device for different positions of an X-ray source on the source guide rail or from different sources. X-ray beam 610 is at normal incidence on the imaging device while X-ray beams 612 and 614 are at oblique incidence. The X-ray beams form the focal surface 136. When an X-ray beam is incident on the imaging device at oblique incidence the image becomes distorted. The distortion may be corrected in the digital X-ray image so that it does not interfere with the process of radiotherapy target detection FIG. 7 shows an embodiment of this invention with a cylindrically curved imaging device 718. In this case X-ray beam 710 is incident at the middle of the imaging device. X-ray beam 712 is incident on the right part of the imaging device 731. X-ray beam 714 is incident on the left part of the imaging device 730. The X-ray beams 710, 712, and 714 correspond to different positions of a source on the source rail or different sources. All three beams strike the imaging device at normal incidence thus eliminating magnification distortion. An imaging device with spherical curvature can also be used to compensate for vertical movement of an X-ray source.

A diagnostic imaging unit, item 134 in FIG. 3, is comprised of a diagnostic X-ray source and an associated imaging device. This invention includes several alternative diagnostic imaging unit configurations. A single imaging device may be used with multiple sources. For example, the left source 124 and right source 125 in FIG. 3 are incident on a single imaging device 118. In this case the two sources are imaged at different times. Alternatively, different sections of the imaging device are used to image the left and right source concurrently. In another embodiment of this invention, referring to FIG. 6, imaging device 118 is divided into a left part 630 and right part 631. These parts may be separate imaging devices that can be positioned independently to optimally image the associated source. It is part of this invention to use multiple diagnostic X-ray sources and multiple imaging devices that can be positioned independently.

Figure 8:
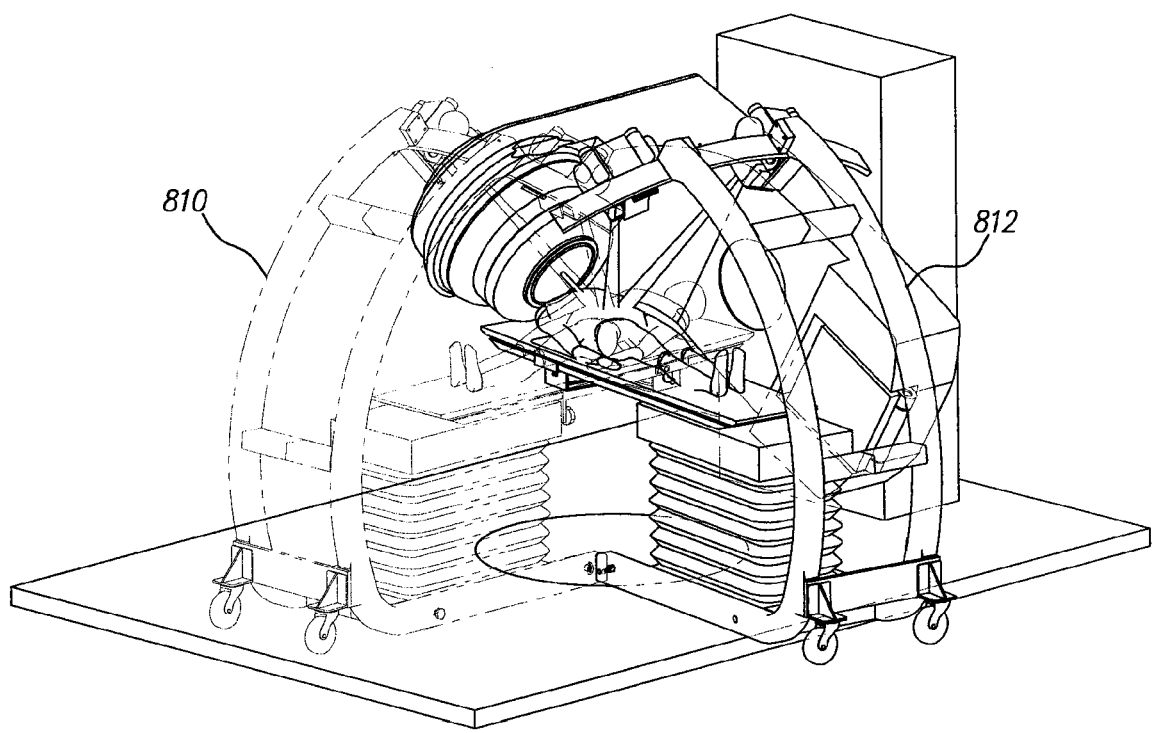
FIG. 8 is an isometric view of source and imaging device assemblies and treatment couch in two positions.
Figure 9A:
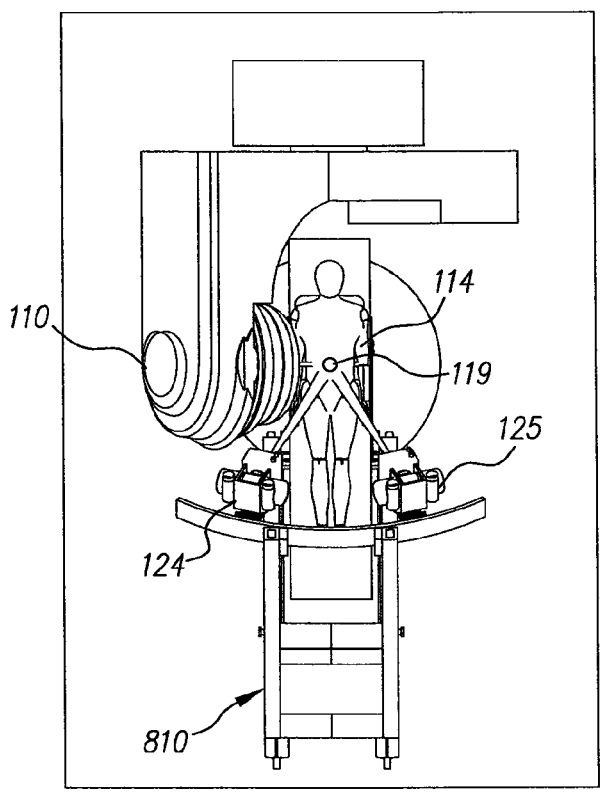
FIG. 9A is an overhead view of source and imaging device assemblies and treatment couch in a first position.
Figure 9B:
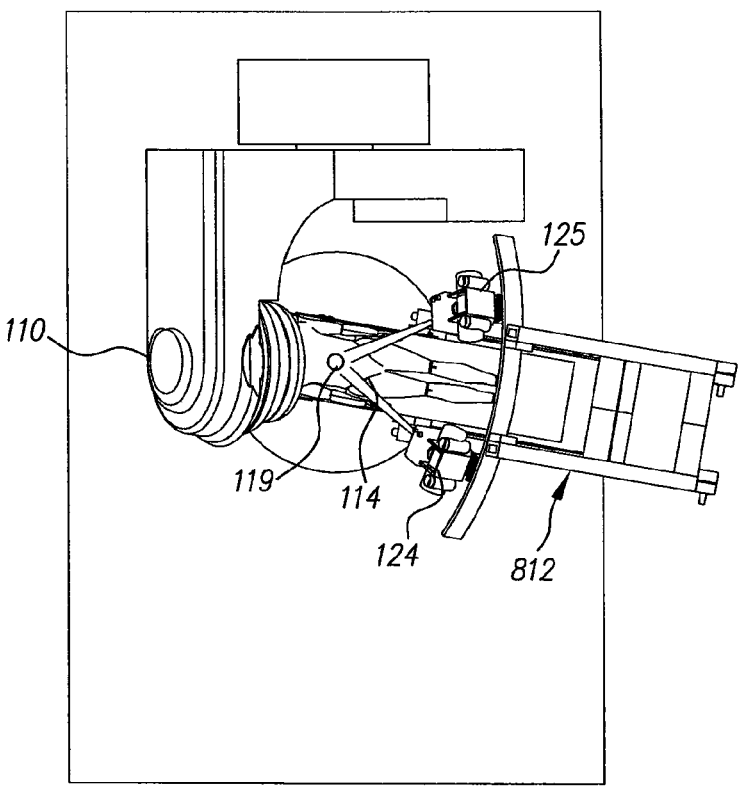
FIG. 9B is an overhead view of source and imaging device assemblies and treatment couch in a second position.

FIG. 8 shows an isometric view of the X-ray source assembly and imaging device assembly connected to the treatment couch in a first position 810 and second position 812. FIGS. 9A and 9B provide an overhead view of the assemblies and treatment couch in position 810 and 812, respectively. These figures illustrate that the position of the X-ray sources 124 and 125 and imaging device 118 remain unchanged relative to the patient 114 when the position of the treatment couch 116 is changed. Furthermore, the radiotherapy target 119 remains in the field of view of the diagnostic imaging units in both positions of the treatment couch. When an X-ray source and imaging device are arranged, relative to the patient, in a desired configured for which detection of the radiotherapy target 119 is facilitated the method of this invention maintains this desired configuration for both positions of the treatment couch. As described in commonly-assigned copending U.S. patent application Ser. Nos. 11/039,422 and 11/221,133, the desired image capture configuration is determined based on a three-dimensional image of the patient. These figures show only two couch positions but it should be understood that the method of this invention is applicable to all couch positions that are used in radiotherapy treatment.

Figure 10A:
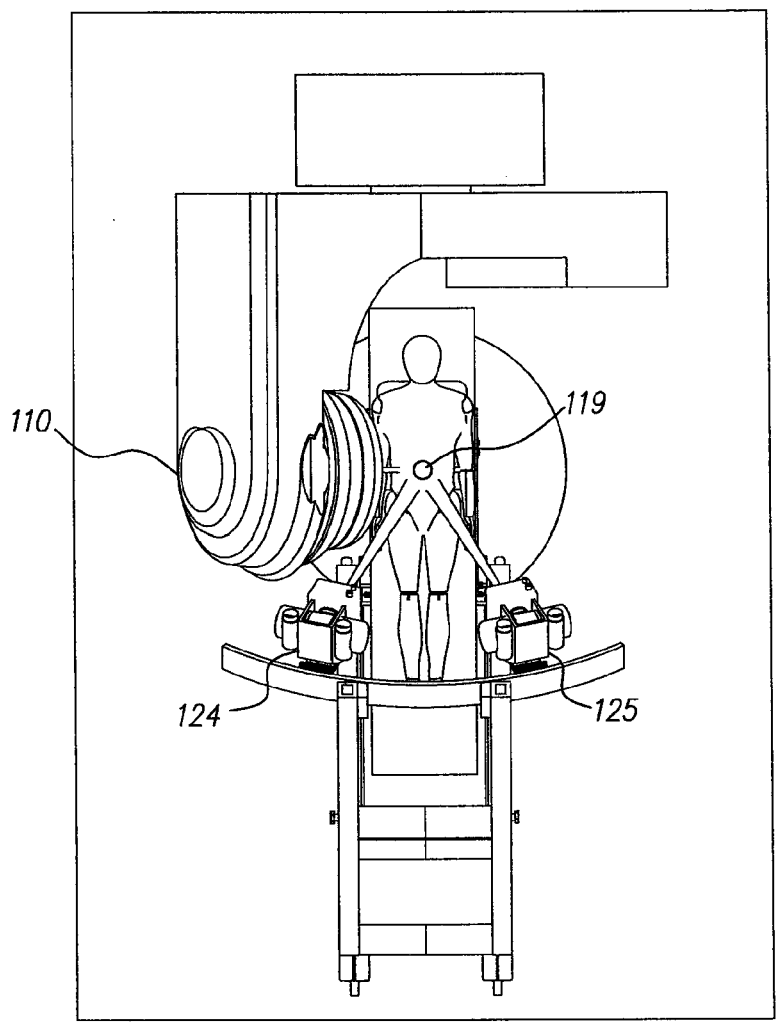
Figure 10B:
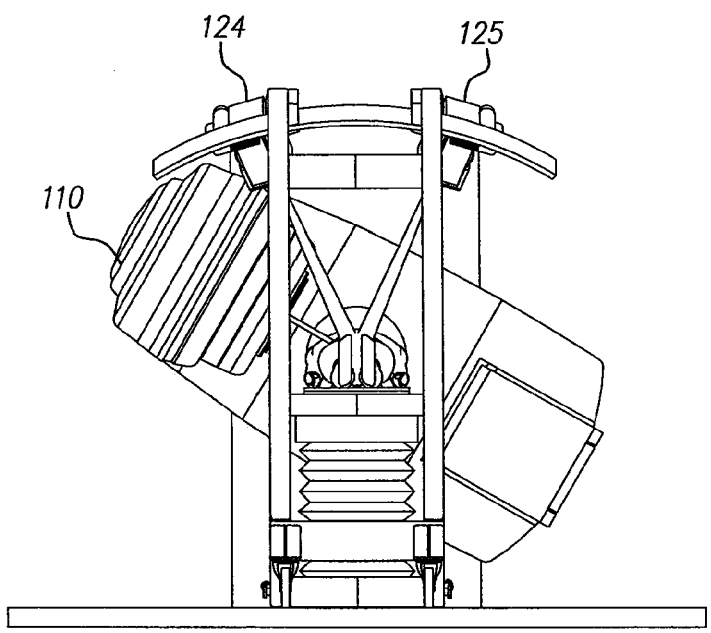
Figure 11A:
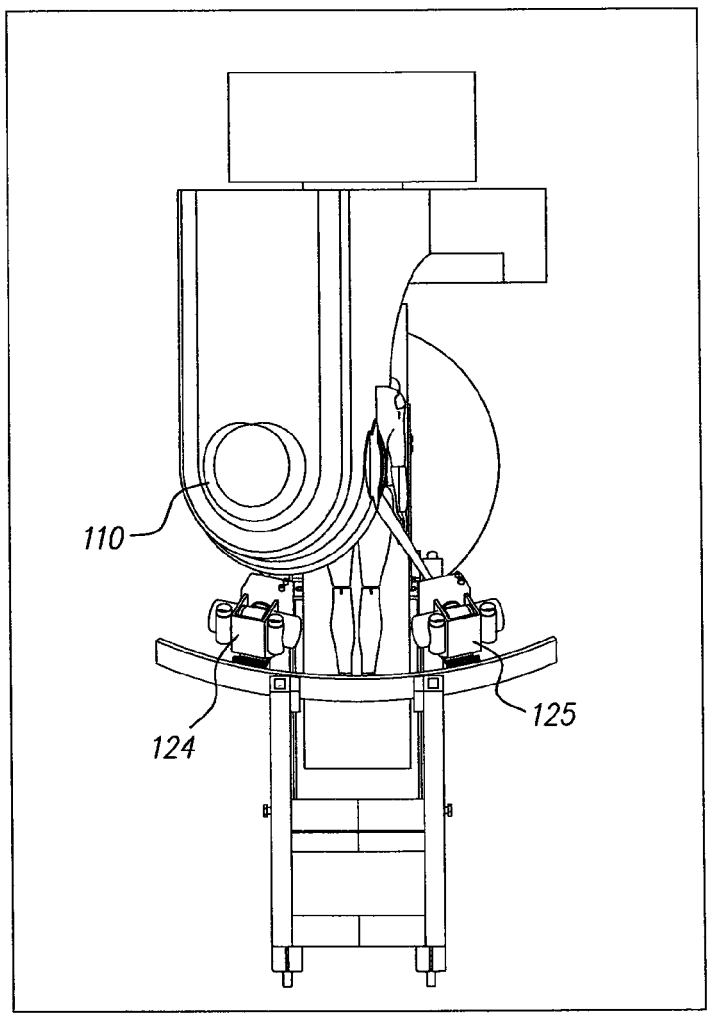
Figure 11B:
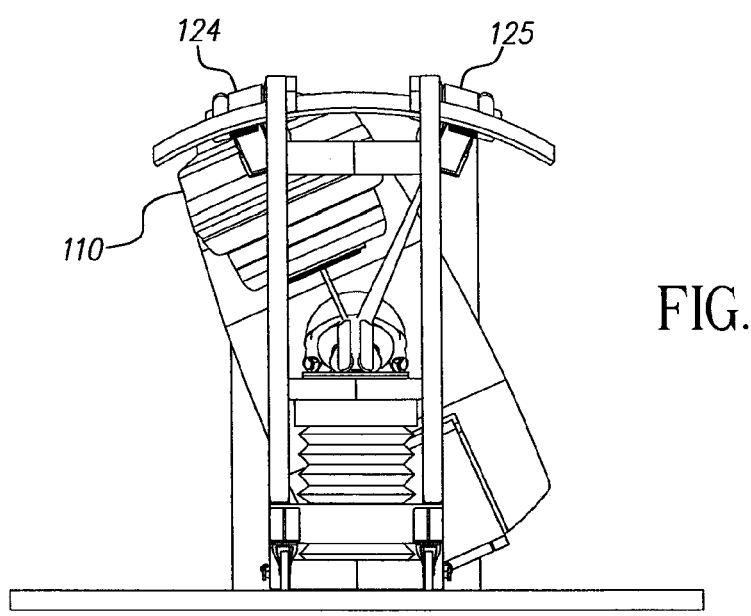
Figure 12A:
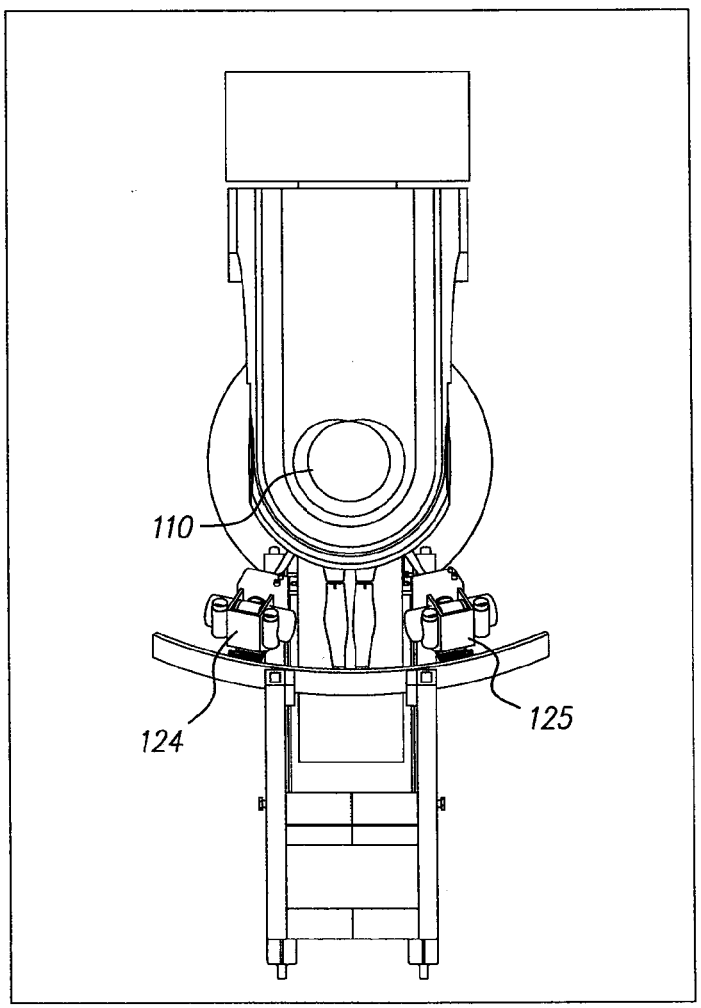
Figure 12B:
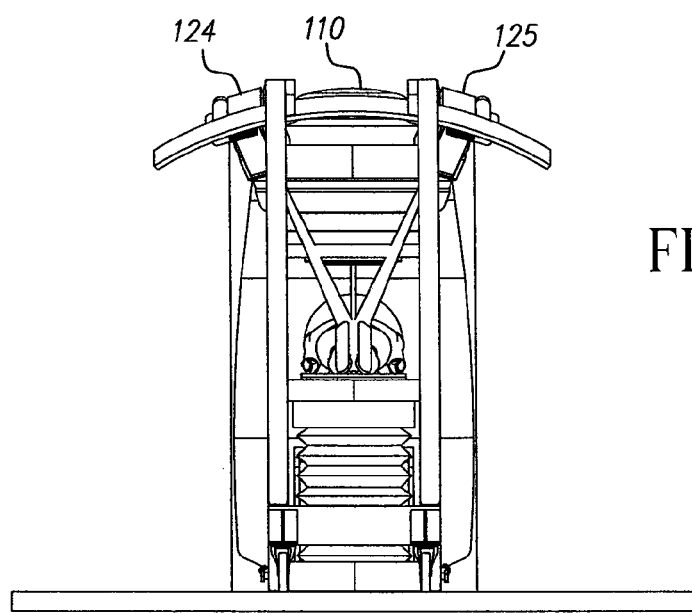
Figure 13A:
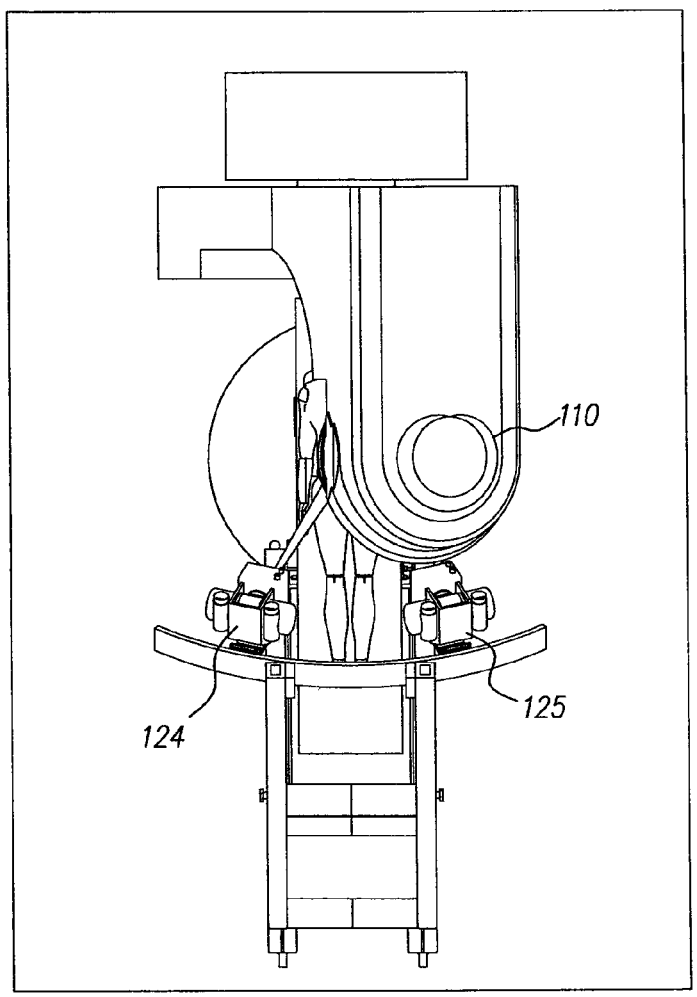
FIG. 13A is an overhead view of radiotherapy system with left diagnostic X-ray source turned on and right source turned off.
Figure 13B:
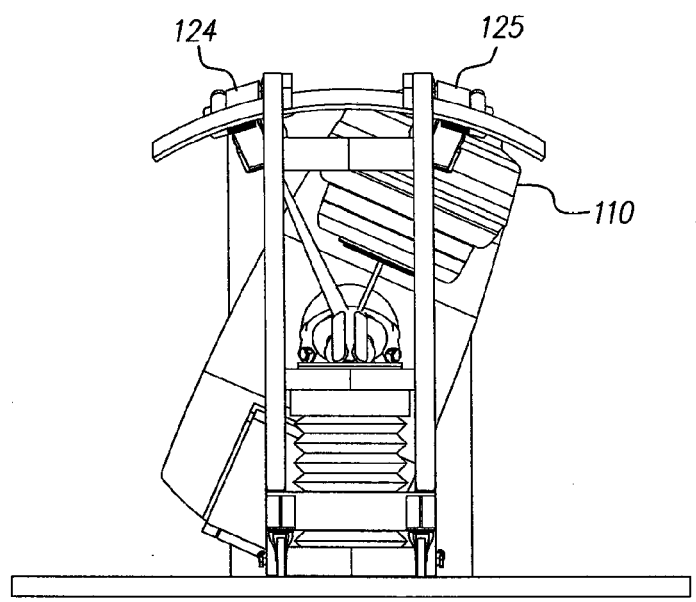
FIG. 13B is a frontal view of radiotherapy system with left diagnostic X-ray source turned on and right source turned off.
Figure 14A:
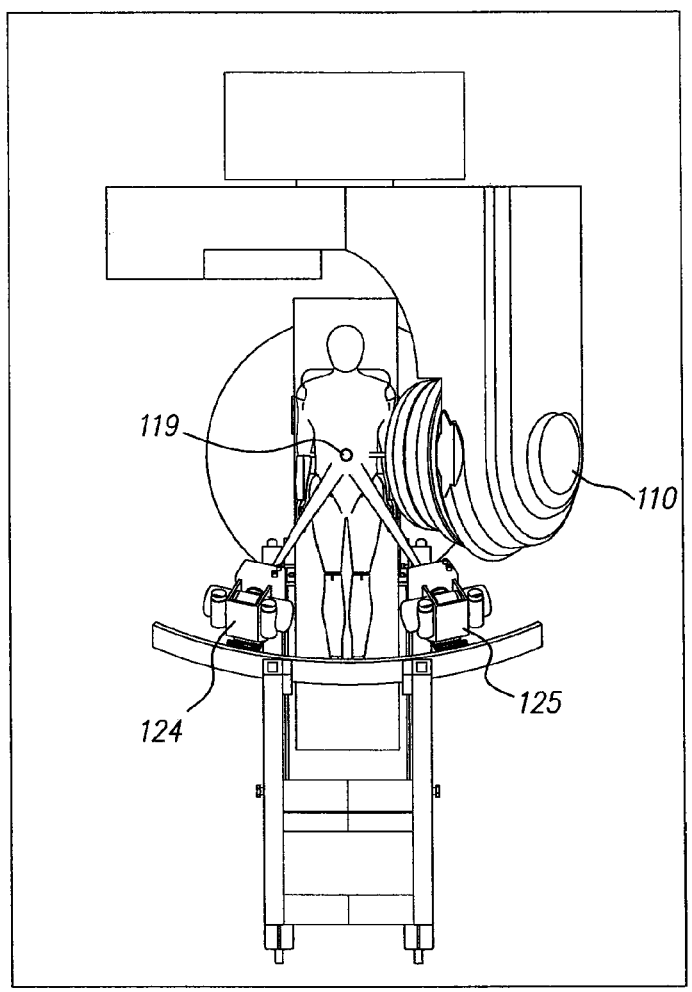
Figure 14B:
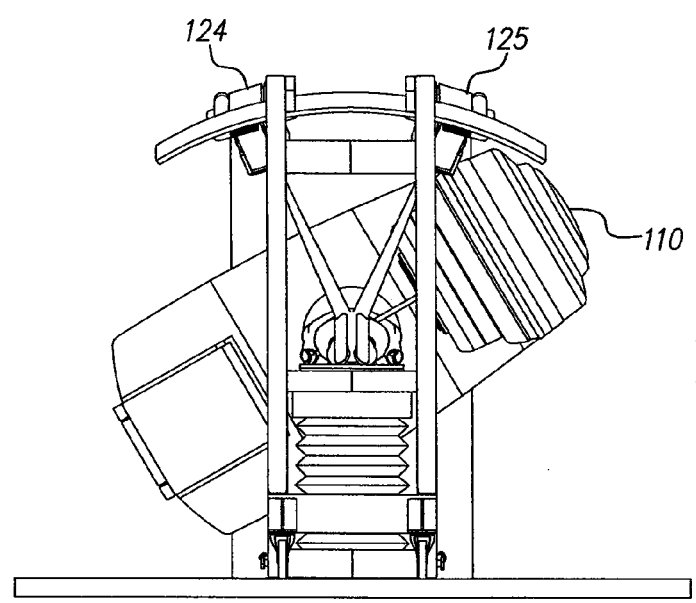

A difficulty that is encountered when incorporating diagnostic X-ray sources and imaging devices into a radiotherapy system is that as the radiotherapy gantry moves it may block a diagnostic X-ray beam or collide with an X-ray source or imaging device. It is desirable to image the target with two separate sources in order to localize the source in three dimensional space. However, if one source is blocked the other can still be used to localize the target in a plane. FIG. 10A shows an overhead view and FIG. 10B shows a frontal view in which the radiotherapy gantry 110 is rotated 60 degrees counter-clockwise. In this case both the left 124 and right 125 sources can be used to create an image of the target on the imaging device 118 (not shown). FIGS. 11A and 11B show a view in which the gantry is rotated 24 degrees counter-clockwise. In this case the blocked left source 124 is turned off and the target is only imaged with the right source 125. In FIGS. 12A and 12B the radiotherapy gantry 110 is in an upright position and the left source 124 and right source 125 are not blocked and can be used to image the target. FIGS. 13A and 13B show the gantry with a clockwise rotation of 24 degrees and the right source 125 blocked. FIGS. 14A and 14B show the gantry with a clockwise rotation of 60 degrees and both sources unblocked.

Figure 15:
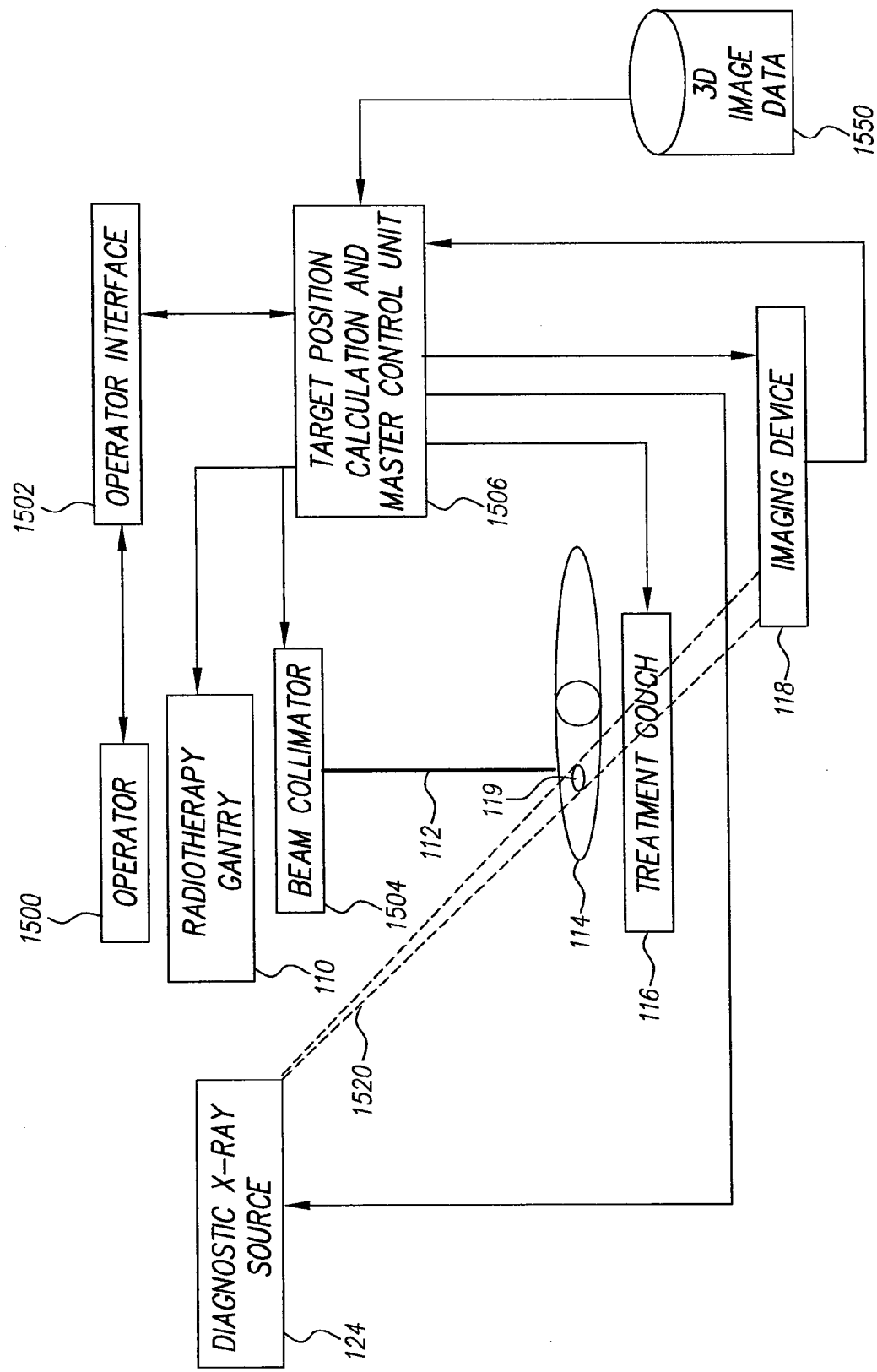
FIG. 15 is a diagram of a target detection control system.

FIG. 15 shows the control system for a radiotherapy system with target detection. In the planning stage a three-dimensional image 1550 is captured of patient 114 in a region that includes the radiotherapy target 119 for therapeutic radiation. The three-dimensional image data is input into the target position calculation and master control unit 1506 which calculates the desired location of the diagnostic X-ray sources 124 and 125 (not shown) for which the radiotherapy target 119 is detectable in images captured by imaging device 118. The master control unit moves the diagnostic X-ray source to a location relative to the patient laying on treatment couch 116 to the desired location. The master control unit may also move imaging device 118 in order to optimally image the diagnostic X-ray sources.

Referring to FIG. 15, at the start of a treatment field operator 1500 asks the patient 114 to commence a breath hold. Using interface 1502 the operator causes a radiograph of the radiotherapy target 119 to be captured by the diagnostic imaging unit consisting of diagnostic X-ray sources 124 and 125 and imaging device 118. Shown in FIG. 15 is a diagnostic X-ray beam 1520 from source 124 that passes through the region surrounding the radiotherapy target and is incident on imaging device 118. The master control unit 1506 processes the radiograph and determines if the target is at the correct location relative to the linear accelerator gantry 110 and beam collimator 1504. If the location of the target is not correct the master control unit disables the application of therapeutic radiation 112. Otherwise, the operator proceeds with applying a radiation dose to the target region. The operator may also cause the master control unit to capture radiographic images during application of therapeutic radiation to verify that the target is in the correct position. Alternatively, the master control unit automatically captures images to verify target location. In an embodiment of this invention, the master control unit automatically stops radiation treatment based on the result of the target location process.

In another embodiment of this invention, referring to FIG. 15, the master control unit 1506 moves the treatment couch 116 in order to place the radiation treatment target 119 in patient 114 into the correct location relative to treatment beam 112 based on the results of target detection. Alternatively, the master control unit moves the beam collimator 1504 in order to displace the treatment beam to the correct location to treat the target.

Figure 16:
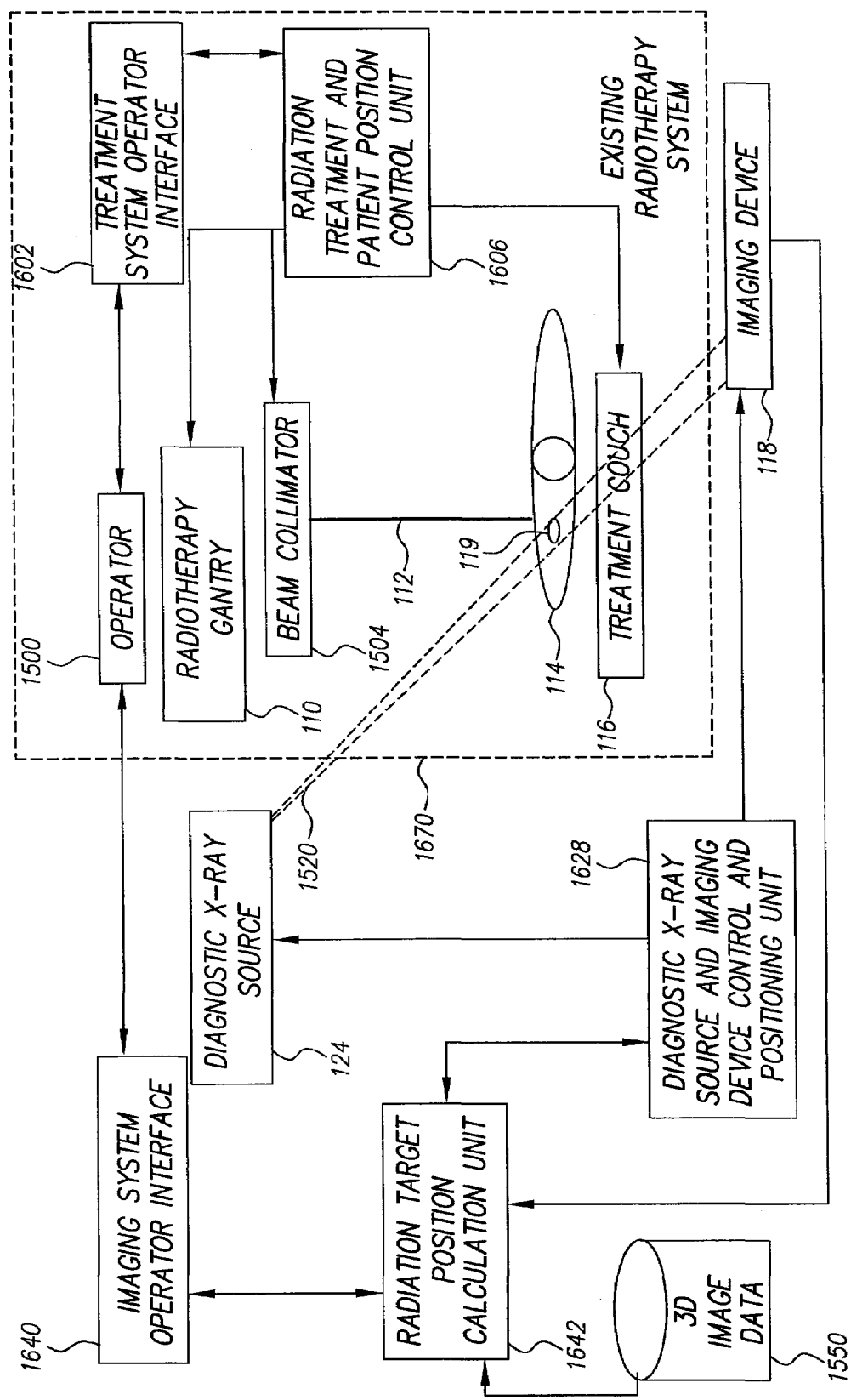
FIG. 16 is a diagram of a target detection control system that is added to an existing radiotherapy system.

FIG. 16 is a diagram of a target detection control system that is added to an existing radiotherapy system. The existing radiotherapy system 1670 includes a radiotherapy gantry 110 with beam collimator 1504, a treatment couch 116, a radiation treatment and patient position control unit 1606, and a treatment system operator interface 1602. The operator 1500 monitors radiation treatment through the interface and video cameras that are mounted in the treatment room (not shown). The target detection system that is added to the radiotherapy system includes a radiation target position calculation unit 1642 which uses three-dimension image data 1550 of a region in patient 114 that includes radiation therapy target 119 to calculate a location of diagnostic X-ray sources 124 and 125 and imaging device 118, relative to the patient, for which detectability of the target is facilitated. The diagnostic X-ray source and imaging device control and positioning unit 1628 moves the diagnostic X-ray source and the imaging device into the desired location and captures radiographic images. The imaging system operator interface 1640 provides to the operator the results of target detection including target location, shape, size, and other target characteristics. The treatment system operator interface 1602 provides the operator 1500 with a means to input target position information into the radiation treatment and patient position control unit 1606. In an embodiment of this invention, the radiation target position calculation unit 1642 communicates directly with the radiation treatment and patient position control unit 1606 for the purpose of gating radiation treatment or providing information on target location that is used to move the treatment couch or therapeutic beam using the collimator 1504 in order to correctly treat the target.

The invention has been described in detail with particular reference to certain preferred embodiments thereof, but it will be understood that variations and modifications can be effected within the scope of the invention.

PARTS LIST 110 radiotherapy gantry
112 therapeutic radiation beam
114 patient
116 treatment couch
118 imaging device
119 radiotherapy target
120 floor pivot
122 X-ray source frame
124 left diagnostic X-ray source
125 right diagnostic X-ray source
126 X-ray source guide rail
130 threaded hole for side locating feature
131 retractable pin for axial locating feature
132 imaging source frame rear wheel
134 diagnostic imaging unit
136 focal surface
210 gantry rotation axis
212 radiotherapy isocenter
214 treatment couch rotation axis
216 diagnostic imaging source beam
218 diagnostic imaging source rotation axis
310 imaging source frame font wheel
312 diagnostic X-ray source isocenter
410 diagnostic X-ray source tilt pivot
412 diagnostic X-ray source focus carriage
414 diagnostic X-ray source vertical carriage
450 first position of diagnostic X-ray source
451 second position of diagnostic X-ray source
460 first position of diagnostic X-ray beam
461 second position of diagnostic X-ray beam
470 first position of imaging device
471 second position of imaging device
505 imaging device assembly
510 imaging device angular adjustment
512 imaging device linear adjustment knob
514 treatment couch top
516 X-ray transparent window
520 X-ray beam
610 X-ray beam
612 X-ray beam
614 X-ray beam
630 left imaging device
631 right imaging device
710 X-ray beam
712 X-ray beam
714 X-ray beam
718 curved imaging device
730 left curved imaging device
731 right curved imaging device
810 sources, imaging device, and couch in first position
812 sources, imaging device, and couch in second position
1500 operator
1502 operator interface
1504 beam collimator
1506 target position calculation and master control unit
1520 diagnostic X-ray beam
1550 3D image data
1602 treatment system operator interface
1606 radiation treatment and patient position control unit
1628 diagnostic X-ray source and imaging device control and positioning unit
1640 imaging system interface
1642 radiation target position calculation unit
1670 existing radiotherapy system

The invention claimed is:

1. A method of delivering therapeutic radiation to a radiotherapy target in a patient positioned on a treatment couch comprising the steps of:
   connecting a first diagnostic X-ray source to said treatment couch wherein said diagnostic X-ray source faces a first side of said patient;
   connecting a first imaging device to said treatment couch wherein said imaging device faces a second side of said patient;
   wherein said first diagnostic X-ray source and said imaging device maintain a desired view of the radiotherapy target with movement of said treatment couch while said first diagnostic X-ray source and said imaging device are connected to said treatment couch during said movement; and
   wherein said patient is in a fixed position relative to said treatment couch.

2. A method as in claim 1 wherein said radiotherapy target is within a field of view of a diagnostic imaging unit comprised of said first diagnostic X-ray source and said imaging device.

3. A method as in claim 2 wherein said radiotherapy target remains within the field of view of said diagnostic imaging unit for two or more positions of movement of said first diagnostic X-ray source.

4. A method as in claim 3 wherein said first diagnostic X-ray source movement is along an arc.

5. A method as in claim 2 wherein said radiotherapy target remains within the field of view of said first diagnostic imaging unit for more than one position of said treatment couch.

6. A method as in claim 1 wherein said diagnostic X-ray source is connected to said treatment couch by means of a frame.

7. A method as in claim 6 wherein said diagnostic X-ray source is movable with respect to said frame.

8. A method as in claim 7 comprising the additional step of: moving said diagnostic X-ray source to a desired position relative to said patient for which said radiotherapy target is detectable in a captured radiographic image.

9. A method as in claim 8 wherein a desired position of said diagnostic X-ray source is determined based on a three-dimensional image of said patient.

10. A method as in claim 7 in which said imaging device has means to adjust position and angle with respect to said first diagnostic X-ray source.

11. A method as in claim 6 in which said frame is removable from said treatment couch.

12. A method as in claim 6 wherein locator means positions said frame in a fixed location relative to said treatment couch.

13. A method as in claim 1 in which said imaging device has a curved surface.

14. A method as in claim 1 further comprising: connecting a second diagnostic X-ray source to said treatment couch.

15. A method as in claim 14 wherein said second diagnostic X-ray source and said imaging device move in lockstep with movement of said treatment couch.

16. A method as in claim 14 wherein said second diagnostic X-ray source and a second imaging device move in lockstep with movement of said treatment couch.

17. A method as in claim 1 further comprising the step of determining said desired view of said diagnostic X-ray source based on a predetermined three-dimensional image of said patient.

18. A method of delivering therapeutic radiation to a radiotherapy target in a patient positioned on a treatment couch comprising the steps of:
- connecting a diagnostic X-ray source to said treatment couch wherein said diagnostic X-ray source faces a first side of said patient;
- connecting an imaging device to said treatment couch wherein said imaging device faces a second side of said patient;
- adjusting a position of said diagnostic X-ray source relative to said patient to obtain a desired view of said radiotherapy target;
- moving said diagnostic X-ray source and said imaging device to maintain the desired view of the radiotherapy target with movement of said treatment couch while said first diagnostic X-ray source and said imaging device are connected to said treatment couch during said movement; and
- wherein said patient is in a fixed position relative to said treatment couch.

19. An apparatus for delivering therapeutic radiation to a radiotherapy target to a patient positioned on a treatment couch comprising:
- a diagnostic X-ray source connected to said treatment couch all on a first side of said patient;
- an imaging device connected to said treatment couch on a second side of said patient;
- wherein said diagnostic X-ray source and said imaging device maintain a desired view of the radiotherapy target with movement of said treatment couch while said first diagnostic X-ray source and said imaging device are connected to said treatment couch during said movement; and
- wherein said patient is in a fixed position relative to said treatment couch.

* * * * *